United States Patent [19]
Baylor, Jr.

[11] Patent Number: 4,863,647
[45] Date of Patent: Sep. 5, 1989

[54] PROCESS FOR PREPARATION OF ELECTROPHORESIS GEL MATERIAL

[76] Inventor: Charles Baylor, Jr., 2720 Grubb Rd., Wilmington, Del. 19810

[21] Appl. No.: 223,875

[22] Filed: Jul. 25, 1988

Related U.S. Application Data

[62] Division of Ser. No. 625,840, Jun. 28, 1984.

[51] Int. Cl.$^4$ .............................................. B29C 35/02
[52] U.S. Cl. ...................................... 264/22; 264/41; 522/3; 522/84; 522/85; 521/50.5; 521/149; 521/150; 521/56
[58] Field of Search ................. 522/3, 84, 85; 264/22; 521/50.5, 149, 150

[56] References Cited

U.S. PATENT DOCUMENTS

| | | | |
|---|---|---|---|
| 2,875,047 | 2/1959 | Oster | 522/84 |
| 3,097,096 | 7/1963 | Oster | 522/84 |
| 3,279,919 | 10/1966 | Faridon et al. | 522/84 |
| 3,549,366 | 12/1970 | Yorgerum | 522/84 |
| 4,133,942 | 1/1979 | Coupek et al. | 521/149 |
| 4,189,370 | 2/1980 | Boschetti | 204/299 |
| 4,190,713 | 2/1980 | Kraemer | 521/149 |
| 4,192,727 | 3/1980 | Ward | 522/84 |
| 4,204,928 | 5/1980 | Via | 523/3 |
| 4,218,356 | 8/1980 | Evans | 522/84 |
| 4,249,685 | 2/1981 | Beede et al. | 522/84 |
| 4,306,955 | 12/1981 | Neel et al. | 522/84 |
| 4,704,198 | 11/1987 | Ebersole | 521/50.5 |

FOREIGN PATENT DOCUMENTS

| | | | |
|---|---|---|---|
| 0584381 | 6/1959 | Canada . | |
| 0969887 | 6/1975 | Canada | 204/103 |

OTHER PUBLICATIONS

A. Chrambach and D. Rodbard, (Sep. Sci., 7, 663–703, 1972).
B. J. Radola, Ed., "Electrophoresis", (1979), Walter De Gruyter, New York, (1980), pp. 79–94, B. J. Radola, A. Kinzkofer, and M. Frey in: R. C. Allen and P. Arnaud, Eds., Electrophoresis 1981, Walter De Gruyter, New York (1981), pp. 181–189, A. Gord, W. Postel, R. Westemeier, E. Gianazza, and P. G. Righetti, ibid., pp. 259–270.

Primary Examiner—Morton Foelak

[57] ABSTRACT

Describes a process for controlling the polymerization and cross-linked density of electrophoretic gel products useful for separation of bioorganic molecules, which process utilizes photoinitiation. Photoinitiated polymerized gels afford the desired advantages of being ultra thin and having a high electrophoretic resolution with programmable porosity profiles.

4 Claims, 7 Drawing Sheets

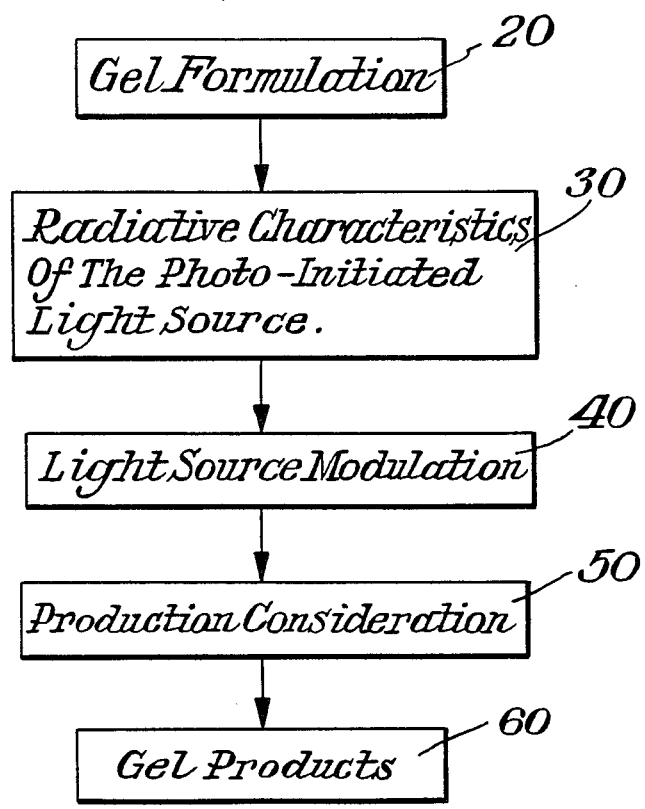

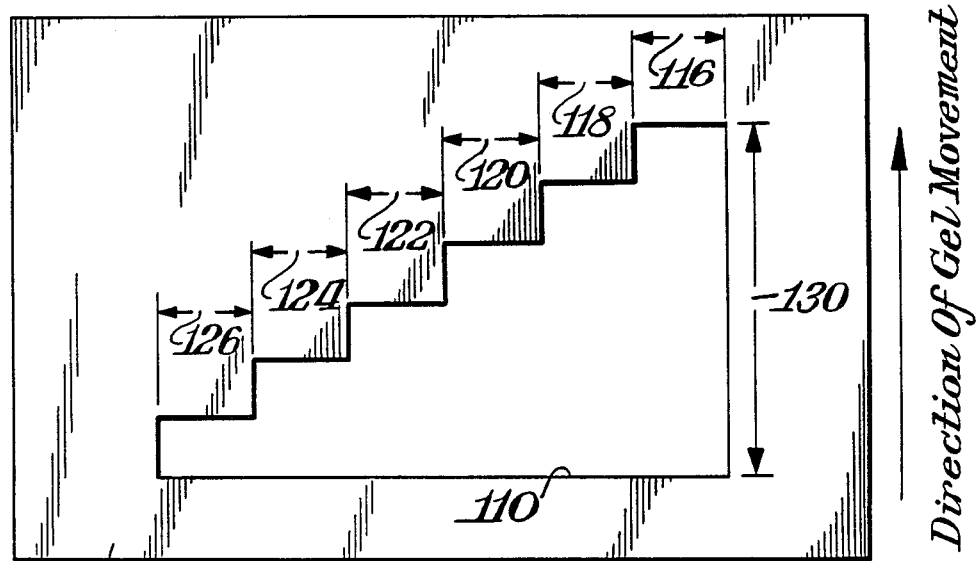
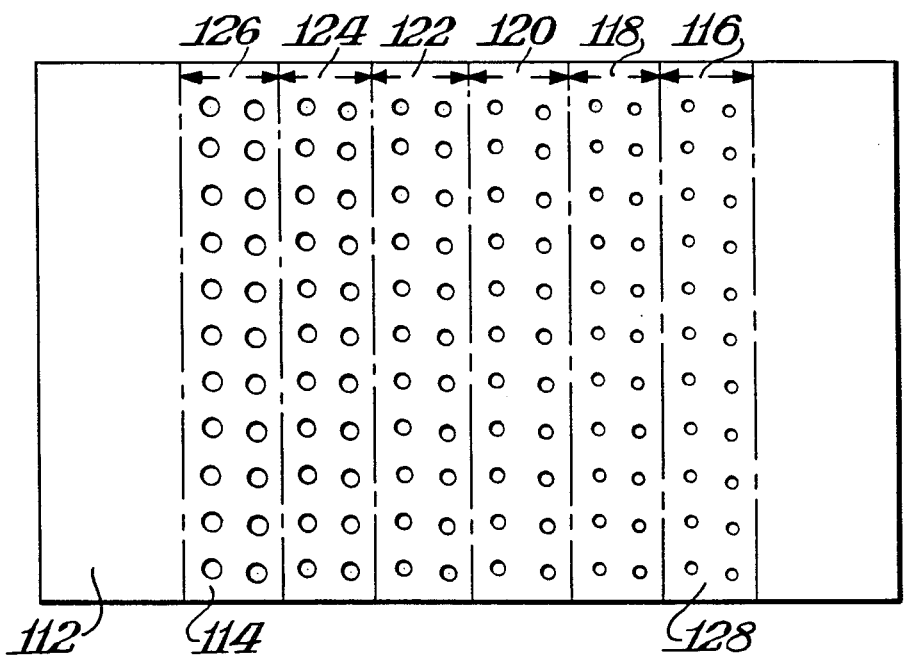

130

132

134

136

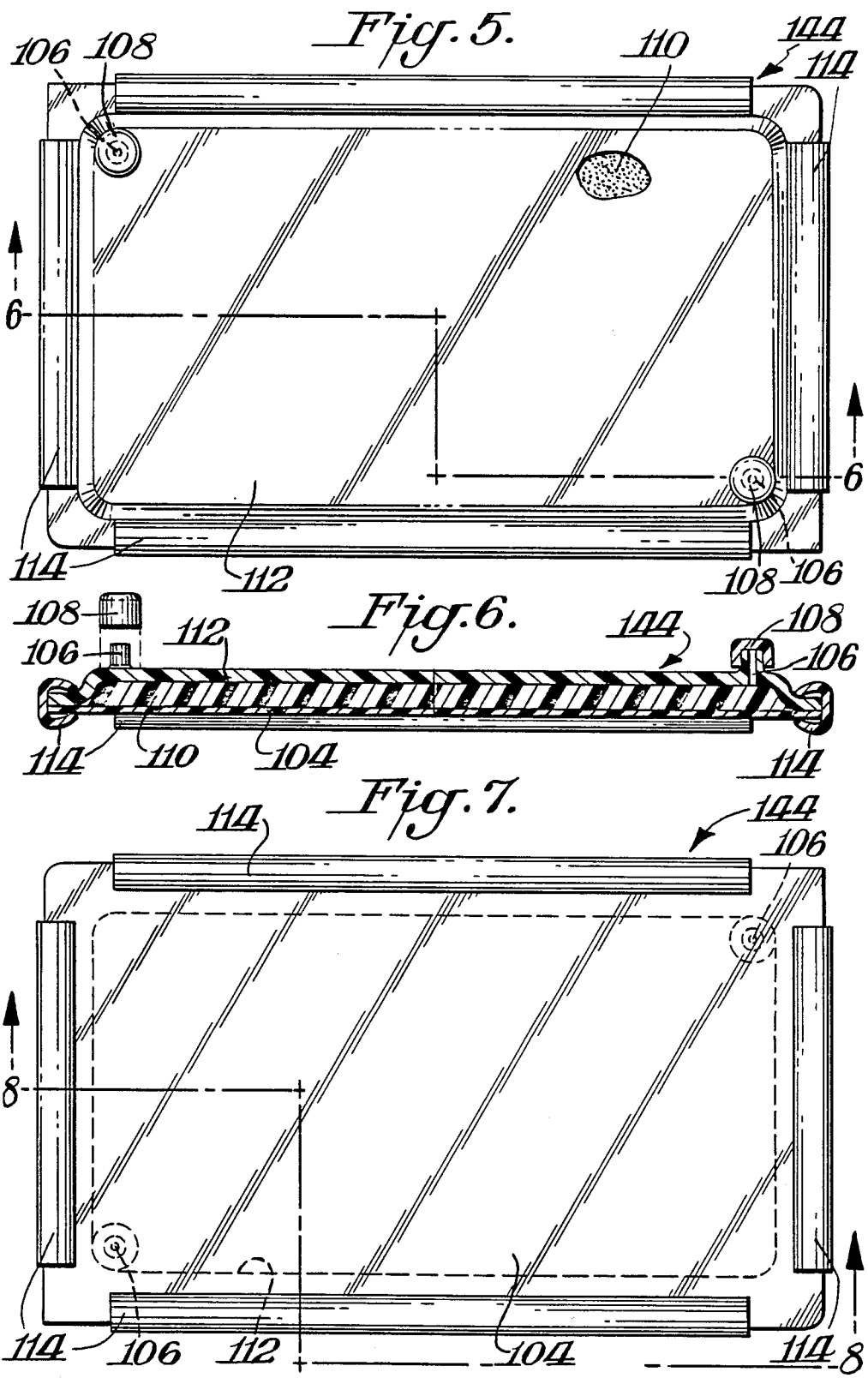

PROCESS FOR PREPARATION OF ELECTROPHORESIS GEL MATERIAL

This is a division of application Ser. No. 625,840, filed June 28, 1984.

FIELD OF THE INVENTION

This invention relates to electrophoretic gel products of controlled cross-link density, useful for separation of bioorganic molecules, and to photopolymerization processes for their production.

BACKGROUND OF THE INVENTION

Electrophoresis is based on the principle that charged molecules or substances will migrate when placed in an electric field. Since proteins and other biopolymers (e.g., DNA, RNA, enzymes and carbohydrates) are charged, they migrate at pH values other than their isoelectric point. The rate of migration depends, among other things, upon the charge density of the protein or biopolymer and the restrictive properties of the electrophoretic matrix. The higher the ratio of charge to mass the faster the molecule will migrate.

Many support media for electrophoresis are in current use. The most popular are sheets of paper or cellulose acetate, silica gels, agarose, starch, and polyacrylamide. Paper, cellulose acetate, and thin-layer silica materials are relatively inert and serve mainly for support and to minimize convection. Separation of proteins using these materials is based largely upon the charge density of the proteins at the pH selected and in general do not provide high resolution separations.

On the other hand, starch, agarose and polyacrylamide gel materials not only minimize convection and diffusion but also actively participate in the separation process. These materials provide a porous medium in which the pore size can be controlled to approximate the size of the protein molecules being separated. In this way, molecular sieving occurs and provides separation on the basis of both charge density and molecular size.

The extent of molecular sieving is thought to depend on how closely the gel pore size approximates the size of the migrating particle. The pore size of agarose gels is sufficiently large that molecular sieving of most protein molecules is minimal and separation is based mainly on charge density. In contrast, polyacrylamide gels can have pores that more closely approximate the size of protein molecules and so contribute to the molecular sieving effect. Polyacrylamide has the further advantage of being a synthetic polymer which can be prepared in highly purified form.

The ability to produce a wide range of gel pore sizes and to form pore size gradients within the gel are additional advantages of polyacrylamide. Control over pore size enables mixtures to be sieved on the basis of molecular size and enables molecular weight determinations to be performed. These determinations are especially accurate if the proteins are coated with a detergent such as sodium dodecyl sulfate (SDS) which neutralizes the effects of molecular charge. This technique is referred to as SDS-PAGE electrophoresis. However techniques shown in the prior art for preparing SDS Electrophoresis gels doe not hield a highly reproducible product.

PORE GRADIENT GELS

Polyacrylamide gels can be made with a gradient of increasing acrylamide concentration and hence decreasing pore size. These gels are now used extensively instead of single concentration gels, both for analysis of the protein composition of samples and for molecular weight estimation using SDS as a denaturing agent to render the proteins in a uniform charge environment. The current techniques used to produce gradient gels are both expensive and require great care to insure somewhat reproducible gradients.

Step gradients in which gels of different concentration are layered one upon the other have been used. Unfortunately, they tend to give artifactual multi-component bands at the interface between layers which creates inaccuracies in the protein mixture determination. It is now common to use continuous acrylamide gradients. The usual limits are 3 to 30% acrylamide in linear or nonlinear gradients with the particular range chosen depending upon the size of the proteins to be fractionated. During electrophoresis in gradient gels, proteins migrate until the decreasing pore size impedes further progress. Once this "pore limit" is approached the protein banding pattern does not change appreciably with time although migration does not cease completely.

One of the main advantages of gradient gel electrophoresis is that the migrating proteins are continually entering areas of gel with decreasing pore size such that the advancing edge of the migrating protein zone is retarded more than the trailing edge, resulting in a marked sharpening of the protein bands. In addition, the gradient in pore size increases the range of molecular weights which can be fractionated simultaneously on one gel. Therefore a gradient gel will not only fractionate a complex protein mixture into sharper bands than is usually possible with a gel of uniform pore size, but also can permit the molecular weight estimation of almost all the components.

Pore gradient gels are conventionally prepared by mixing high and low concentration monomer solutions in order to produce a concentration gradient of acrylamide in the gel molds. These techniques incorporate elaborate pumping schemes which must be operated with great care to insure the desired gradient. Also, these techniques are time consuming and expensive and do not lend themselves to reproducible production techniques.

In addition to the gradient in acrylamide concentration, a density gradient of sucrose or glycerol is often included to minimize mixing by convective disturbances caused by the heat of polymerization. Some workers avoid the latter problem by including a gradient of polymerization catalyst to ensure that polymerization occurs first at the top of the gel and then proceeds to the bottom. Gradient gels prepared by any of these methods generally display poor reproducibility.

The polyacrylamide gel so prepared results from polymerization of acrylamide and simultaneous polymer cross-linking by bifunctional compounds such as N,N'-methylene-bis-acrylamide (BIS). The most prevalent method of initiation of polymerization is through the use of sodium or ammonium persulfate an and accelerator N,N,N',N'-tetramethylethylenediamine (TEMED). Acrylamide plymerization can also be accomplished photochemically using riboflavin. However, riboflavin initiated polymerization requires an intense UV or visible light source which must be applied for periods of 30 minutes to several hours depending upon the intensity and wavelength of the source. Further detrimental to its use is the fact that it undergoes a rapid photobleaching reaction which reduces its concentration and changes it to a noninitiating form, so that achievement of high monomer conversion to polymer is difficult.

Photoinitiation with riboflavin is characteristically nonreproducible both because of the long duration of the exposure required with attendant uncertainty about complete polymerization and the chemical instability of riboflavin. Photoinitiation of polymerization as described in the prior art does not allevaite the problems of constructing pore-gradient gels by mixing different concentrations of monomer liquids. In fact, the slow rate of polymerization with riboflavin and prolonged exposure with intense light sources only seems to exaggerate the effects of convective mixing in destroying the design and reproducibility of the pore-gradient.

A. Chrambach and D. Rodbard (Sep. Sci. 7, 663–703, 1972) cited the acceleration of riboflavin photoinitiated polymerization by addition of the accelerator TEMED. For good control of the reaction, however the system also required persulfate be present. This system as with ribloflavin alone does not alleviate the problems of constructing pore-gradient gels by mixing different concentrations of monomer. In both cases, riboflavin alone or with added accelerator (TEMED) and persulfate, oxygen inhibits the radical polymerization and monomer mixtures must be degassed prior to initiation.

The details of the preparation and the use of such gels for electrophoresis are generally and comprehensively reviewed by B. D. Hames in B. D. Hames and D. Rickwood, Eds., "Gel Electrophoresis of Proteins", pp. 1–89, IRL Press, Washington, D. C. (1981).

pH GRADIENT GELS (IEF)

Amphoteric materials (low molecular weight ampholytes) can be added to gel formulations. Following polymerization, the ampholyte materials migrate in the electric field according to their pI (isoelectric points) and come to rest in zones in the order of their pI. A pH gradient is thus produced in the gel.

Further details of IEF separations are described by B. An der Lan and A. Chrambach, in B. D. Hames and D. Rickwood, "Gel Electrophoresis of Proteins", pp. 157–186, IRL Press, Washington, D.C. (1981).

Note that much of the general literature describe gels of 500 $\mu$m to 1500 $\mu$m thickness. However, selected works do disclose thin and ultrathin gels in the range of 20 $\mu$m to 500 $\mu$m thicknesses. B. J. Radola and references therein, in: B. J. Radola, Ed., "Electrophoresis '79", Walter De Gruyter, New York (1980), pp 79–94 discuss ultrathin-layer isoelectric focusing in 50–100 $\mu$m polyacrylamide gels (no gradient) prepared by casting on silanized glass or polyester sheets. B. J. Radola, A. Kinzkofer, and M. Frey in: R. C. Allen and P. Arnaud, Eds., "Electrophoresis '81", Walter De Gruyter, New York (1981), pp 181–189 describe isoelectric focusing in ultrathin-layer (20–50 $\mu$m) polyacrylamide gels. No discussion appears as to the gel preparation. A. Gorg, W. Postel, R. Westermeier, E. Gianazza, and P. G. Righetti, ibid., pp. 259–270 also describe isoelectric focusing and gradient electrophoresis in 240–360 $\mu$m thick poly-acrylamide gels. The gels are cast vertically, one at a time, by gradient mixing of solutions to form the pore-size gradient. Advantages of ultrathin gels are discussed. Gradients of pore size are achieved only after great difficulty for thin gels using the methods of the prior art. As a result the advantageous features of thin gels have not been widely used in the prior art.

Gels prepared by any of the above processes can suffer from several disadvantages which can compromise their utility in polyacrylamide gel electrophoresis (PAGE) and in isoelectric focusing (IEF). Unreacted polymerization initiator which is present can react with biological molecules and cause distorted separations or sample decomposition. The present polar inorganic initiators (persulfate/TEMED) can increase background staining and thus decrease contrast of background with sample spots. The initiator systems described herein are advantageous in that they do not react or associate with biological molecules, mainly because they are organic in nature, not readily soluble in the case of heterogeneous initiators. These initiators also show no problems with staining and destaining of the gels.

In general, the electrophilic gels prepared using the various prior art methods suffer from many disadvantages. Among these, the presence of various initiators in a gel often caused random reactions of the initiator with free monomer, buffers or acrylamide polymer. Furthermore, the inorganic initiator or its by-products may react with the protein samples themselves, thereby distorting the electrophoretic results. Because of the ineffective mechanical blending of reagents and uncontrolled reactions, the gels produced by the techniques of the prior art are neither accurate nor are they highly reproducible. Another problem encountered with the prior art techniques is that because of the thermal convection, vibration, mixing and capillary action, it is relatively difficult to produce thin gels, i.e., those less than 500 $\mu$m in thickness. Further, these prior art techniques tend to be relatively expensive since they are batch-type operations and labor-intensive.

SUMMARY OF THE INVENTION

According to the present invention, a porous gel product useful for electrophoretic separations is obtained. This product is characterized by the presence of a photoinitiator or a hydrogen donor and is stable, reproducible and has a controlled electrophoretic porosity. Polymerization is initiated by homogeneous photopolymerization using water soluble organic photoinitiators or heterogeneous photopolymerization in which the organic initiator is suspended or dispersed in the aqueous photopolymerization solution and is controlled to produce the desired pore gradient. The gel product consists essentially of polyacrylamide and water, but may also contain acrylamide, agarose, bis-acrylamide, and other monomers or polymers. Buffers or ampholytes, detergents and solutes may also be included in the formulations. The formulations are polymerized and cross-linked in a defined manner which may be mathematically defined for a specific use. Gel products may vary in thickness from 50 82 m to 2 mm with the 100–300 $\mu$m range being most preferred.

Preferably the gel product consists of an aqueous-swelled porous matrix formed from polymerized and cross-linked acrylamide monomers. The concentration of acrylamide monomers in the solutions from which gels are made is essentially from about 3% (weight/volume) to about 30% (weight/volume), and about 0.3 to 1.2% weight/volume of a water-soluble or water dispersible components of a photoinitiating system. The gel products may have length, width and thickness dimensions and the pore size of the gels may be in the form of a gradient, which may vary along any of the length and width dimensions and may be in a linear, or a complex function of pore size.

According to the method of this invention, charged bioorganic molecules are electrophoretically separated using the gel product by the steps of placing a sample of bioorganic molecules on a thin plate of the gel product and applying a voltage across a dimension of the product. This gel product also has length, width, and thickness dimension and has a porosity gradient along one of the dimensions.

A process for preparing a porous gel product useful for electrophoretic separation by the steps of, forming a water solution or dispersion of a mixture from about 3% weight/volume to about 30% weight/volume of acrylamide monomer and a cross-linking agent, the cross-linking agent comprising about 2% weight/weight to about 15% weight/weight of the total monomer; adding a free radical generating system that absorbs light and initiates polymerization of the monomers; forming the solution into the shape of the desired gel products; and subjecting the formed solution to light radiation to polymerize and cross-link the monomer solution.

The free radical generating system (photoinitiating system) consists essentially of aqueous soluble or dispersible compounds that include [mono and dicarbonyl compounds, Michler's ketone [4,4'-bis(dimethylamino)-benzophenone], 4-carboxybenzophenone, benzophenone, 9,10-phenanthrenequinone 3-sulfonate potassium salt, 1,2-napthoquinone-2-sulfonate potassium salt, 1,4-napthoquinone-2-sulfonate potassium salt, 4-trichloromethyl-4-methyl-2,5-cyclohexadienone and other aromatic water soluble or dispersible mono and dicarbonyl compounds; benzoin ethers such as benzoin methyl either and other benzoins and dyes such as methylene blue and new methylene blue.

The mono and dicarbonyl compounds and dyes are used with hydrogen donors consisting of:
N,N-dimethylaminobenzoic acid
N,N-dimethylaminoethanol
N-methyl diethanol amine
Sodium p-toluene sulfinate
Triethanolamine.

The cross-linking agent includes N,N'-(1,2-dihydroxyethylene)-bis-acrylamide, N,N'-methylene-bis-acrylamide (BIS), N,N'-diallyltartramide (DATD), ethylenediacrylate, and N,N'-bis-acrylylcystamine and other cross-linking monomers. For a given composition, the process includes a step of regulating the light intensity applied to the monomer solution to vary porosity. Light intensity is controlled using the array of techniques common to photographic imaging. The flux may be modulated for fixed sheet-like gels by a computer and microprocessor programmed, moving shutter. Alternatively, the light flux can be modified for continuous manufacture by conveying or moving individual gel molds or continuous or undivided gel compositions under gradient neutral density filters, grids, or variable shaped apertures, which modulate the light intensity.

The gel products prepared in the manner described have many advantages, among these are enhanced electro-phoretic properties. For example, the gradient can be versitally programmed and can be accurately and reliably reproduced by photographic imaging techniques. Furthermore, thinner gels are readily produced using the method of this invention as well as custom gels, i.e., gels having any pattern porosity profile desired because the gradient mixing steps are avoided. In general, inexpensive gels may be produced because of the continuous process permitted by the method of this invention. The gels are safer and the user does not have to handle toxic acrylamide, only the packaged gel. Furthermore, the gels manufactured by this invention can enable the application of higher voltages with faster migration times. Additionally, the gel products of this invention have reduced endosmosis flow due to the reduced ionic content of the gel formulation.

BRIEF DESCRIPTION OF THE DRAWINGS

The detailed operation of the method described briefly above can be best understood by reference to the following drawings in which:

FIG. 1 is a block diagram of the method for generating electrophoretic gels via ultra-violet or visible radiation;

FIG. 2 is a top plan view of a stepped exposure gradient slit;

FIG. 3 is a drawing illustrating the resulting gel porosity profile from the stepped exposure gradient slit in FIG. 2;

FIG. 5 is a top plan view of a gel mold and film support;

FIG. 6 is a cross-sectional view in elevation taken along line 6—6 of FIG. 5;

FIG. 7 is a bottom plan view of a gel mold and film support assembly;

DETAILED DESCRIPTION OF THE PREFERRED EMBODIMENT METHOD OF THE INVENTION

Figure 4A:
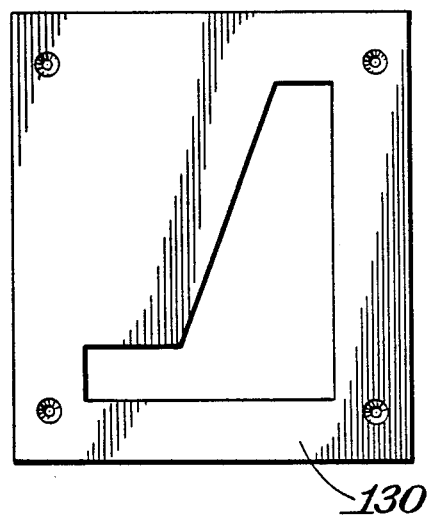
FIG. 4a–d is a drawing illustrating different typical slits used for porosity gradients.
Figure 4B:
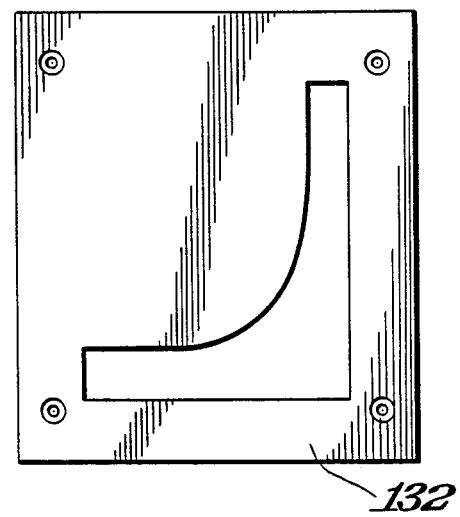
Figure 4C:
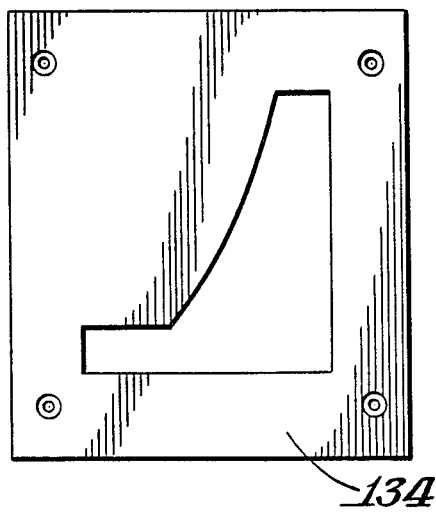
Figure 4D:
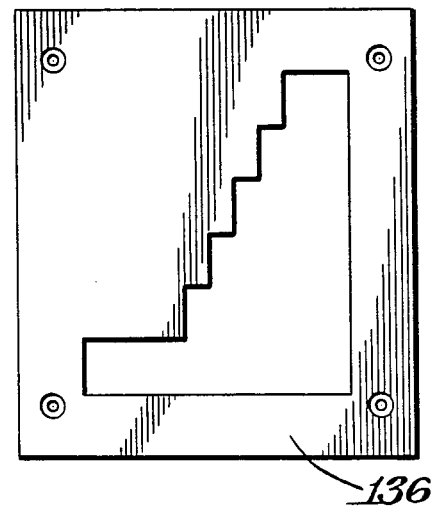
Figure 8:
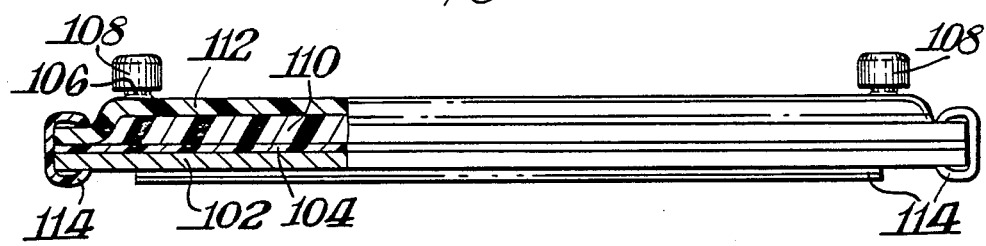
FIG. 8 is a cross-sectional view in elevation taken along line 8—8 of FIG. 7.

The method of the invention, which overcomes many of the difficulties experienced in the prior art, permits one to control the degree of polymerization of a gel to a known reproducible porosity profile. It has been shown in the prior art that inorganic initiators interfere with the separation of some biological molecules which is due to the highly polar nature of the inorganic initiator. This invention utilizes initiators that are organic in nature and therefore are less polar in nature lending to a reduction of interference with said biological molecules. This invention also utilizes light radiation as a means for the initiation of radicals in the gel solution which in turn results in gel polymerization. The degree of polymerization and cross-linking of a given monomer formulation in turn defines the electrophoretic gel separation characteristics which are the key to protein separation in electrophoretic gels. This photopolymerization technology enables the preparation of all types of polyacrylamide electrophoresis gels. This technology enables control over the porosity and electrophoretic properties of the resulting gel materials to a degree which to date has been unobtainable. Using this approach, different types of electrophoresis gels can be successfully developed for a broad range of analytical applications including pore gradient gels for molecular weight determination and pH gradient gels for resolution on the basis of molecular charge and isoelectric point.

Referring to FIG. 1, there is seen the steps of the method of this invention which may be used to produce electrophoretic gel products characterized by a presence of a photoinitiator which consists essentially of an aqueous-swelled porous matrix formed from polymerized and cross-linked monomers whereby the polymerization is initiated by radicals produced by light radiation. In FIG. 1, steps 20 through 60 specifically define these essential elements which in combination provides a unique approach in programming the porosity of a given gel composition. The steps are now described.

First the gel is formulated in step 20 by selecting the gel components which, depending upon the chemical compositions chosen, influence the ability of the gel materials to polymerize and cross-link to yield the desired gel porosity and influence other separation characteristics. In order to establish the exposure parameters for a given gel formulation, it is necessary to determine the radiation characteristics of the light source 30. Once this is determined, the light source is modulated 40 to produce a gradient gel by way of a mask or mechanical shutter, which provides an intensity modifying means, which in turn allows for complex gel porosity patterns to be established.

This ability to control the gel porosity as a function of light radiation produces a stable, accurate and reproducible gradient which can be easily adapted to a continuous manufacturing operation. Therefore, production considerations 50 are warranged. All of the above steps lead to the product 60 of this invention.

GEL FORMULATION 20

When considering manufacturing electrophoretic gels via light radiation in accordance with this invention, the chemical composition considerations, Step 20, are important in order to achieve the desired porosity profile. For instance, the selection of gel materials influences gel characteristics such as the specific or nonspecific binding of proteins or the electro endosmosis.

Acrylamide is the preferred and major monomer used in gel manufacturing; however, other water soluble monomers which can undergo radical initiated polymerization can be used. Other water soluble monomers may be co-polymerized with acrylamide to achieve desired properties. By the process disclosed, certain water soluble polymers can also be used in conjunction with the above monomers or directly to form gel products.

The concentration of the above described monomers in the initial gel formulation and in the final gel products may vary from about 3% wt/v to about 30% wt/v. This range is preferred for reasons of gel stability, strength and porous matrix properties. Gels with a low concentration of acrylamide are the most porous and pass large molecules easily. These are useful in IEF where no restriction of molecules is desired or in separation of large DNA fragments. Gels with a higher concentration of acrylamide are less porous and provide restrictive passage for higher resolution of low molecular weight materials.

Chemical cross-linking can occur in the gels by the presence of suitable polyunsaturated, functional acrylic or allylic compounds.

Compounds which act as suitable cross-linking agents include for example, N,N'-methylene-bis-acrylamide (BIS), N,N'-diallyltartramide (DATD), ethylenediacrylate, N,N'-bis-acrylylcystamine, N,N'-(1,2-dihydroxyethylene)bis-acrylamide and TEOTA (polyoxyethyltrimethylolpropanetriacylate). BIS is preferred for reasons of reactivity, compatability and solubility but other cross-linking agents may be added to or used instead of the BIS. They are added to the initial gel formulation in concentrations of about 0% of the total monomer concentration (wt/wt); to about 10% of the total monomer concentratin (wt/wt); the actual amount being determined by the degree of cross-linking required in the gel and may be determined empirically. The preferred range is about 2 to 7%. If these comonomers are added to the primary acrylamide composition, the concentration of acrylamide may not be less than about 50% of the total monomer concentration.

The total monomer concentration of the initial formulation (including cross-linking agent) on a weight percent/volume basis is expressed as % T. The concentration of the cross-linking monomer is expressed as a wt/wt percentage of the total monomer concentration and is called % C.

The gel formulations may be modified by the addition of polymeric materials compatible with the electrophoretic separation technique. Such compounds include but are not limited to agarose, agar-agar, and polyacrylamide (of varying molecular weights). The compounds may be added to modify viscosity, porosity and gel strength. They can be added to the formulation in concentrations ranging from about 0% wt/v to about 20% wt/v, the preferred range is determined empirically on the basis of each individual gel product.

Water soluble polymers that may be useful individually or as co-components in gel formulation include polyacrylamide, polyvinylpyrrolidone, polyethylene oxide, polymethylvinylether, polyvinyl-alcohol and agarose.

The initial gel formulation and hence the final gel itself may be further modified by the addition of varying concentrations of buffers, detergents, denaturants, ampholytes, and solutes. Buffer systems used are dependent on the final end use of the gel product. Typical examples of individual buffers, used in aqueous systems, include tris-(hydroxymethyl) aminomethane (TRIS)hydrochloric acid, citric acid, sodium hydrogen phosphate, and borates. Buffers may be used individually or in combination to insure proper buffering capacity and ionic strength. The concentrations and mixtures used in such buffer systems are selected on the basis of final end-use and are obvius to one skilled in the art. Details may be found in general references such as Hames and Rickwood.

Detergents may be added to gel formulations or directly to the bioorganic sample to be separated. In both cases, the detergent is added to solubilize the sample or to maintain a uniform charge to mass ratio so that samples separate solely on the basis of size. Detergents and their concentrations are selected empirically on the basis of gel product end-use and on the basis of sample type to be separated. Detergents which may be used include, for example, cetyltrimethyl ammonium bromide, cetylpyridinium chloride, deoxycholate, sodium dodecyl sulfate (SDS), polyethylene oxide sorbitan monooleate and ethoxylated octylphenols. General references such as Hames and Rickwood treat in detail the use of such detergents.

If the gel products are to be utilized for IEF separations, ampholytes must be added to the gel formulation. Ampholytes are amphoteric electrolytes added to IEF gels to generate the pH gradient necessary for IEF separation. The ampholytes sold commercially are generally complex mixtures of polybasic amines and polyacids. There are no limitations imposed by the instant invention on the type or concentration of ampholytes added to the instant gel products. References such as Hames and Rickwood clearly define the limitations of ampholytes inherent in all gel mixtures.

The initial gel formulations of the instant invention may or may not be degassed by inert gas (nitrogen, argon, helium, etc.) purging to remove dissolved oxygen prior to casting. The use of high intensity light radiation for polymerization generates a high level of radicals, rapidly depletes dissolved oxygen and thus obviates the usual need to rigorously exclude oxygen from the initial gel formulation as long as sample preparation and exposure conditions remain constant and consistent. However, during exposure a cover sheet is necessary to prevent inhibition of polymerization due to atmospheric oxygen, which can be rapidly replenished by diffusion.

Once mixed, the initial gel formulation may be modified with further additives, if desired, and then is placd in a casting mold or simply between two cover sheets. Details of the casting are described later under production considerations 60.

Several photoinitiators, i.e., free-radical generating systems that are characterized by producing gels with excellent resolving and destaining properties, are presented in Table 1.

TABLE 1

| Formulation No. | Initiator System Components for 20T, 5C gels | gms[a] | %[b] | Gel[c] Time (sec) |
|---|---|---|---|---|
| 1 | 4-carboxy-benzophenone | 0.45–0.90 | 0.11 | 25 |
|   | triethanolamine | 2–4 | 0.5–1.0 |   |
| 2 | 4-carboxy-benzophenone | 0.45 | 0.11 | 35–50 |
|   | 4-dimethylamino benzoic acid | 2–4 | 0.5–1.0 |   |
| 3 | 4-carboxy-benzophenone | 0.45 | 0.11 | 20–90 |
|   | N,N—dimethyl-aminoethanol | 2–4 | 0.5–1.0 |   |
| 4 | 4-carboxy-benzophenone | 0.45 | 0.11 | 20–30 |
|   | N—methyl diethanolamine | 2–4 | 0.5–1.0 |   |
| 5 | 4-carboxy-benzophenone | 0.45 | 0.11 | 15 |
|   | Sodium paratoluene sulfinate | 4 | 1.0 |   |
| 6 | 9,10-phenanthrenequinone-2-sulfonate potassium salt | 0.4 | 0.1 | 60 |
| 7 | 9,10-phenanthrenequinone-2-sulphonate potassium salt | 0.4 | 0.1 | 25 |
|   | triethanolamine | 4.0 | 1.0 |   |
| 8 | 9,10-phenanthrenequinone-2-sulfonate potassium salt | 0.4 | 0.1 | 25 |
|   | sodium paratoluene sulfinate | 4.0 | 1.0 |   |
| 9 | 9,10-phenanthrenequinone-3-sulfonate potassium salt | 0.4 | 0.1 | 60 |
|   | sodium paratoluene sulfinate | 4.0 | 1.0 | 10 |
|   | 1,2-napthoquinone-4-sulfonate-potassium salt | 0.4 | 0.1 | 50 |
|   | sodium paratoluene sulfinate | 4.0 | 1.0 | 11 |
|   | 1,4-napthoquinone-2-sulfonate potassium salt | 0.4 | 0.1 | 40 |
|   | sodium paratoluene sulfinate |   |   |   |
| 12 | benzoin methyl ether | 0.4 | <0.1 | 30 |
|   | ethanol | 20 | 5 |   |
| 13 | new methylene blue | 0.1 | 0.025 | 30[d] |
|   | sodium paratoluene sulfinate | 4.0 | 1.0 |   |
| 14 | methylene blue | 0.1 | 0.025 | 15[d] |
|   | sodium paratoluene sulfinate | 4.0 | 1.0 |   |

Legend
[a] gms of component/100 ml of solution
[b] % w/volume, gel solution
[c] exposed w/2 kw mercury photopolymer source (Berkey Ascor Co.) Gel times are for uniform gels.
[d] gel thermally unstable; polymerized without light; not useful for gradient gels.

It may be seen in the above table that using a two kilowatt mercury photopolymer light source can produce a gel at exposure time as short as 15 seconds, depending upon the initiator and hydrogen donor combination used.

RADIATIVE CHARACTERISTICS OF LIGHT SOURCE 30 AND LIGHT SOURCE MODULATION 40

In order to successfully control the porosity across an electrophoretic gel product, the uniformity of the resultant radiated pattern must be known.

This pattern must be taken into consideration in designing the slits, neutral density filters or shutter program to compensate for nonuniformity. The technique used to establish the above characteristics are well known in the art. For example devices such as a spectral radiometer, can be used to gather exposure distribution information as a function of a given X,Y coordinate.

In the present invention the preferred light source is ultra-violet having an output between 300–400 nm. This correlates best with the photoinitiators that are preferred. Actually any light source that will activate the initiators to produce polymerization can be used. The preferred radiation source used was a long-wave UV lamp made by Cole-Parmer Instruments consisting of two 15 watt self-filtering black-light blue tubes which produces a 108° beam and a typical intensity of 1100 μW/cm² of 365 nm light at 0.5" from the light housing. Another source successfully used in polymerization of gel solutions was a 2 kw Addalux mercury photopolymer lamp with output from 300–600 nm. With the latter source the gels were located 4 inches (about 10 cm) from the lamp housing. The gel time for this source was 15 sec. Gel time with the black-blue lamp is 30 sec. (2× that of the Hg photopolymer source). The second source has considerable infrared output and continuous exposure longer than 3 min would require cooling of the gel during polymerization.

Once the light source has been characterized, the intensity can be regulated to vary the gel porosity. The regulation is accomplished by modulating the light flux (watts/cm²) as a function of the length, width and thickness of the gel. The flux may be modified for a fixed sheet-like gel by a programmed shutter or a moving conveyor. Where a conveyed web or moving sheet-like gel production operation is desired, such devices as neutral density filters, grids, or variable shaped apertures, may be used to regulate the flux. In a fixed gel production operation, a computer driven shutter, neutral density filter or grids can also be incorporated. More detailed discussion of these devices will be given in the section pertaining to the generation of the exposure gradient.

EFFECTIVE POROSITY (T) AND INTENSITY (I) AS APPLIED TO GEL POLYMERIZATION VIA LIGHT RADIATION

Polyacrylamide electrophoresis gels are cross-linked polymer networks formed by polymerizing solutions normally containing 5–30% total acrylamide monomer in water. Normally 2–7% of the monomer is N,N'-methylene-bis-acrylamide (BIS). This is added to provide cross-links to the matrix. Normally the monomer is chemically polymerized to completion using standard persulfate initiator combinations, or photochemically using riboflavin. The restrictive nature of the gel is related to the percent of total monomer (% T) and the amount of cross-linker present via polymer density and degree of cross-linking.

Literature convention has defined the restrictive nature of a gel in terms of the percent total monomer containing 3% BIS polymerized in the gel. For example, a gel having a "20% T porosity" demonstrates the restrictive character of a gel formed by polymerizing to completion a solution of 20% total acrylamide to which 3% BIS had been added. Therefore, one refers to gels as having 10, 15, 20% T porosity depending on the composition.

This above convention works well in relating the electrophoretic response of the gel formulation since polymerization is assumed to approach completion. In the context of the present invention, the electrophoretic response cannot be related directly to the acrylamide content or % T. This is because both degree and nature of the polymerization process is controlled by the radiation exposure. For example, using photoinitiated radiation polymerization, a range of porosity can be achieved with a given initial formulation by varying the range of exposure. The equivalent porosity of a photoinitiated produced gel can be referred to as an equivalent effective % T, which will be termed T in the content of this disclosure.

GENERATION OF EXPOSURE GRADIENTS

The most common electrophoretic gel performance relationships used in the art is molecular weight versus distance and porosity versus distance profiles. The accuracy by which the porosity can be controlled as a function of distance across a gel is unique allowing for essentially a programmable profile which is dependent upon desired performance relationships. In accordance with this invention, of porosity is controlled via photoinitiation and a gel can be manufactured to the specific needs of a particular researcher.

The generation of the porosity gradient incorporates a radiation flux modifying means for both fixed and conveyed or moving gels. This flux modifying means takes the form of moving shutters, screens, grids, or variable shaped apertures. A typical slit used for porosity gradient production is illustrated in FIG. 2, where depending upon the shape of the slit a given porosity profile is achieved. For example, using a stepped exposure shaped slit as a mask 108 positioned above a gel carried on a conveyor moving under a light source, the light source would polymerize the gel 112 only in the regions of the mask which are open to the gel. If the gel were moved or conveyed relative to the mask and light source, certain regions of the gel would be exposed for a longer length of time, i.e., more exposure. Since exposure is proportional to polymerization and cross-linking, which in turn is proportional to porosity, a pore gradient gel could be produced.

For example, in FIGS. 2 and 3, an electrophoretic gel 112 exposed to light using the stepped slit 110 would have porosity gradients in step fashion across the lanes 116 through 126. Lane 116 would have the highest degree of polymerization corresponding to a smaller pore size 128, since the vertical slit length 130 of lane 116 is the largest of the mask. Lane 126 would correspond to the least polymerized portion of the gel corresponding to a larger pore size 114. Other examples of different exposure gradient masks are illustrated in FIG. 4a, b,c,d, such as a linear 130, polynomial 132, exponential 134, or stepped dose patterns 136.

For fixed or stationary gel exposure, porosity gradients can be created by the use of a programmable shutter assembly which moves across the gel at a prescribed speed. The speed of the shutter as it moves across a gel for a given intensity, and gel composition will determine the porosity profile. A detailed description of the shutter exposure system along with a continuous gel manufacturing process will be discussed in the section describing production considerations 60.

PRODUCTION CONSIDERATION 50

With the system optimized in accordance with the discussion in the previous disclosure, it is entirely feasible to produce gels of a given porosity profile using the batch mode or continuous manufacturing operation.

According to this invention the gel formulations are exposed in two part molds having a polystyrene tray 112 and having a polyester cover sheet 104 which serves as a gel support, as best seen in FIGS. 5, 6, 7 and 8. The trays 112 used in a successful experiment were essentially shallow 4.5"×5" trays, 12 mils (300 μm) deep and contain a series of ridges running about ¾ of the length of the gel dividing it into eight lanes. The trays 112 are covered with 7 mil "Gel Fix" ® polyester film 104 obtained from Serva Feinbiochemica to provide a flexible support for the completed electrophoresis gel. For special 2-D integrated gel application, electrodes are printed on the support film. In this case the lane ridges and sample application wells are removed from the molds.

The polyester film 104 may be sealed to the polystyrene tray 112 by applying a thin coating of Dow Corning silicone high vacuum grease to the edge of the mold and then rolling the two parts together. The grease provides a water-tight liquid seal. The two parts are then clamped together using strips of a plastic edge moldilng 114 for paper bundles (Slide-Lock Binding Bars ®) that are cut into strips the length of the gel. Following exposure, the gel adheres preferentially to the polyester film 104 support and thus can be pealed out of the mold due to the difference in adhesion between the two halves.

Prior to attachment to the tray 112, the polyester film 104 is squeezed onto the plate 102 using water to provide adhesion. The laminate is then attached to the tray 112 using silicon grease and edge clamps as described earlier. The trays 112 are filled through small ports 106 located at opposite corners of the tray 112. The trays 112 are held on an angle to allow air or argon to be displaced by the monomer solution. The ports 106 are capped with small rubber septa 108 and an aluminum plate 102 is pressed into place below film 104 to act as a gel support.

The mold assembly consisting of the gel formulation 110, polyester film 104, tray 112, plate 102 and edge molding 114 such that plate 102 rests directly on the conveyor belt. This device is termed the gel support assembly 144 and is used for gel polymerization regardless of the type of manufacturing process chosen.

Figure 10:
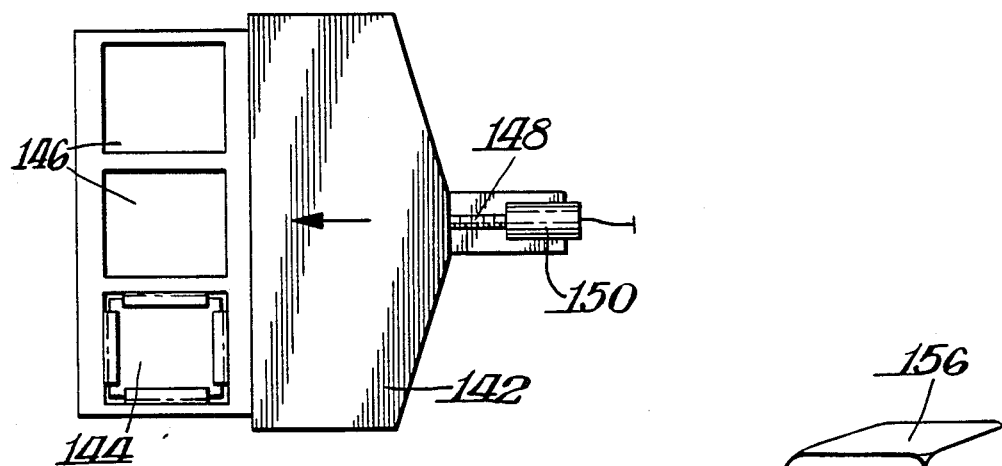
FIG. 10 is a drawing illustrating the top view of a shutter system for use in the manufacturing of electrophoretic gels.
Figure 9:
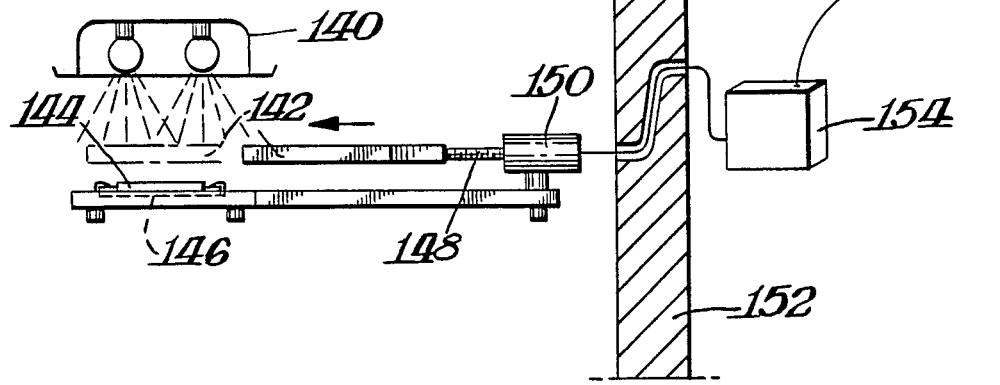
FIG. 9 is a drawing of a shutter system for use in the manufacturing of electrophoretic gels.

Illustrated in FIGS. 9 and 10 is a computer driven shutter device which is capable of producing exposure gradients in a batch type mode. The programmable shutter 142 is placed at that distance below the light source 140, which results in a uniform radiation distribution at the target. The gel support assemblies 144, filled with monomer as described, are then placed in the sample holders 146 such that the fill ports 106 are on the top side of the support assembly 144 2 or 3 abreast (as best seen in FIG. 9.) The programmable shutter 142 is then positioned directly above the support assemblies 144. The light source 140 is then activated and allowed to reach full intensity. The programmable shutter 142 is then activated which starts to open via a screw drive 148 and stepper motor 150 arrangement controlled by the software commands of the computer 156 according to the desired exposure profile. An Intel ® 8255A Programmable Peripheral interface 154 was used to coordinate the analog to digital control communications between the computer and shutter drive system. To isolate the user from the ultra-violet radiation, a radiation cell wall 152 is located between the shutter system and control room. A top view of this apparatus is illustrated in FIG. 10. After exposure is complete the light source is simultaneously cutoff.

Figure 11:
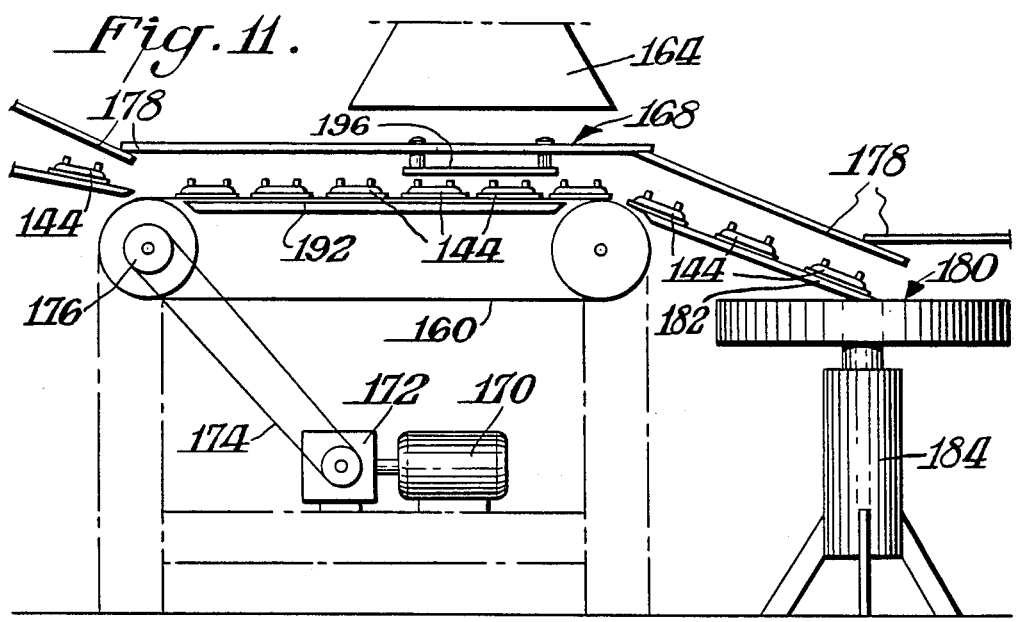
FIG. 11 is a drawing of a conveyor system for use in the manufacturing of electrophoretic gels.

A second device used for gel formulation exposure is a conveyor system for continuous manufacturing of gels, which is illustrated in FIG. 11. The gel support assemblies 144 are filled with monomer by hand and are then placed on a stainless steel conveyor belt 160, which is used to transport the gels to the light source 164 and then on to the collection area 180.

After placing the gel support assemblies 144 on the conveyor belt 160, the light source 164 is activated. When the light has stabilized, the conveyor 160 is started and the gel support assemblies 144 pass under a slit, grid or screen assembly 168 at a constant predetermined belt speed.

Figure 13:
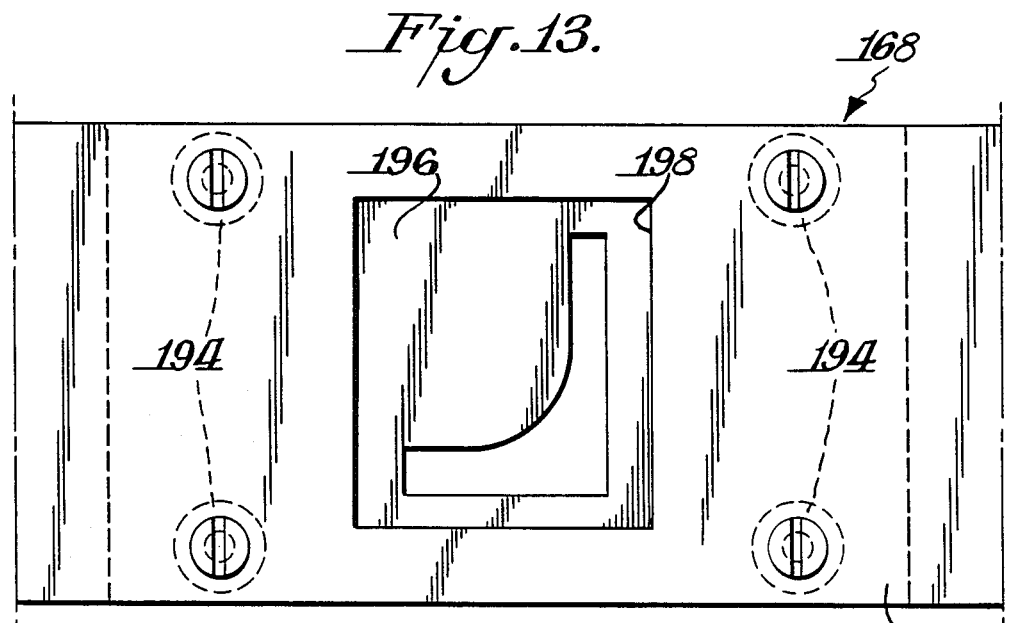
FIG. 13 is a drawing illustrating the top view of the slit shown in FIG. 12.
Figure 12:
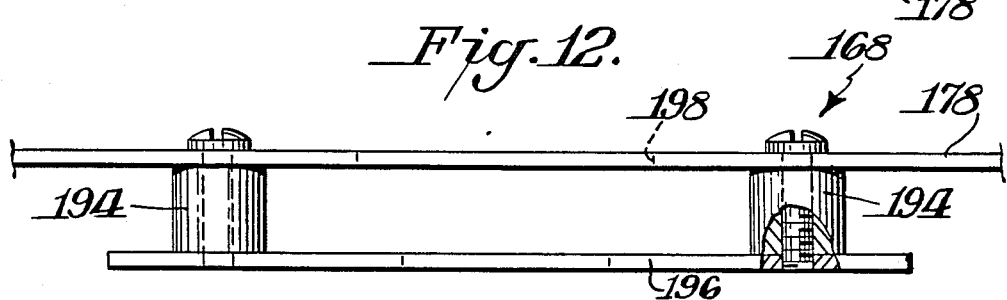
FIG. 12 is a drawing illustrating a typical slit, assembly used during gel irradiation.

An illustration of a typical slit, grid, or screen assembly 168 is shown in FIGS. 12 and 13. The slit mask 196 of interest is chosen depending upon the desired porosity profile required. The slit 196 is coupled to the holder and shield assembly 178, which acts as a retaining means for the light filter of interest along with protecting the gel support assemblies 144 from unwanted light. To allow the passage of the light throughout the slit 196 a window 198 is provided above the slit. The slit 196 is held parallel to the shield assembly 198 via four bushings 194.

The conveyor belt 160 (FIG. 11) is driven by a motor 170, which is coupled to a reduction gear box 172, which drives a belt 174, which in turn drives a belt pulley 176. During exposure the gel support assemblies 144 are protected from unwanted light by the shielding 178, located above the conveyor 160 and sample collection area 180. As the gel support assemblies 144 leave the conveyor 160 they slide down an exit ramp 182 into the sample storage area 180, which can be adjusted vertically by a hydraulic stand 184.

Since the light source produces a constant intensity with constant energy over a defined area at a fixed rate, polymerization is proportional to the time of exposure. Time can be modulated by the programmed shutter movement, or by constant conveyor movement under variable fixed slits cut to dimensions corresponding to the desired gradient.

The calculations of slit dimensions, shutter movement, conveyor beltspeed, and light intensity are all factors which must be determined prior to manufacturing electrophoretic gels using photopolymerization.

Modifications can be made to the conveyor system to provide continuous introduction and removal of samples which are compatible with potential manufacturing processes.

An example of how each of the above manufacturing systems can be used to generate uniform porosity exposures, separate lane porosity variation exposures, and continuous gradient exposures is described below.

UNIFORM EXPOSURES

To produce a uniform exposure using the batch type shutter system, see FIG. 9, the samples 144 are placed on the shutter table 146 so that each portion of the gel 144 is exposed for the same length of time. In the conveyor system FIG. 11, the samples 144 are passed under a square or rectangular slit 196 at constant rate. These two manufacturing methods are subtly different from each other even though they both produce the same overall exposure. With the shutter system, the sample 144 receives essentially a uniform instantaneous exposure over its entire surface area simultaneously initiating polymerization at all points in the gel. With the conveyor system an exposure front passes over the gel producing a corresponding polymerizatin or reaction front, along with its associated diffusion and thermal gradients.

LANE EXPOSURES

To produce a gel with separate lanes having different but uniform exposures using a batch type system, see FIGS. 9 and 10, requires the manual or automatic movement of the shutter 142 across the length of the gel in a stepped fashion to mask the sample in an exposure pattern similar to the one described in FIGS. 2 and 2. The preferred method of producing "lane" exposures is the use of the conveyor system, FIG. 11, with a slit pattern the same as that described in FIG. 2.

CONTINUOUS GRADIENT EXPOSURES

The final kind of exposure used was one to produce exposure gradients corresponding to a specific desired porosity range or limiting molecular weight distribution along the length of the gel in the electrophoresis direction. These gradients were produced using both shutter and variable fixed slits with the conveyor. The use of each will be described.

Using the batach type shutter system, FIGS. 9 and 10, the support assemblies 144 are placed in the sample holders 146. The programmable shutter 142 is then positioned direclty above support assemblies 144. The light source 140 is then activated and allowed to reach full intensity at which time the shutter 142 is opened to produce the desired exposure profile.

The preferred means of exposure is using the conveyor system (FIG. 11), with the use of masks 168 to produce the gradient. The masks 168 are cut in specific patterns required to produce the exposure gradients needed to generate particular molecular weight or porosity versus distance profiles. Sample gels 144 are placed on the conveyor with the electrophoresis direction perpendicular to the direction of the belt movement and then exposed. FIG. 4a–d illustrates different representative mask patterns available to give desired electrophoretic porosity responses.

COATING PROCEDURE

While a casting procedure using molds must be used for making gels from pure water monomer formulations, a continuous coating procedure can be used with solutions that have been thickened using either polyacrylamide or some other compatible, water soluble polymers. Two possible coating techniques will be described. The first utilizes a cover sheet, the second an inert coating-reaction chamber.

Figure 14:
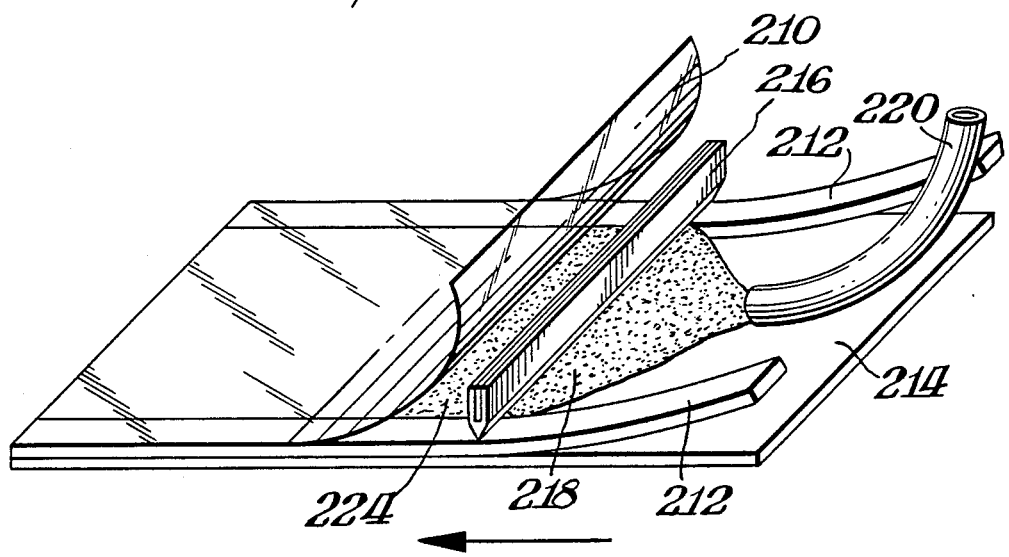
FIG. 14 is a drawing illustrating a continuous coating procedure utilizing a cover sheet.

If the gel formulations are coated at a remote location from the light source, a cover sheet 210 as best seen in FIG. 14, will have to be applied to prevent evaporation of solvent (water) and provide an oxygen barrier for polymerization. The cover sheet 210 may also contain printed electrodes and the like, or these may be included as part of the base. To provide uniform gel thickness, spacers 212 must be used. These are placed on the film support 214 as a template. The monomer-polymer composition 218 is then pumped onto the film support 214 by way of a nozzle 220. A coating knife 216 is used to form the monomer-polymer formulation 218 into a uniform gel.

Figure 15:
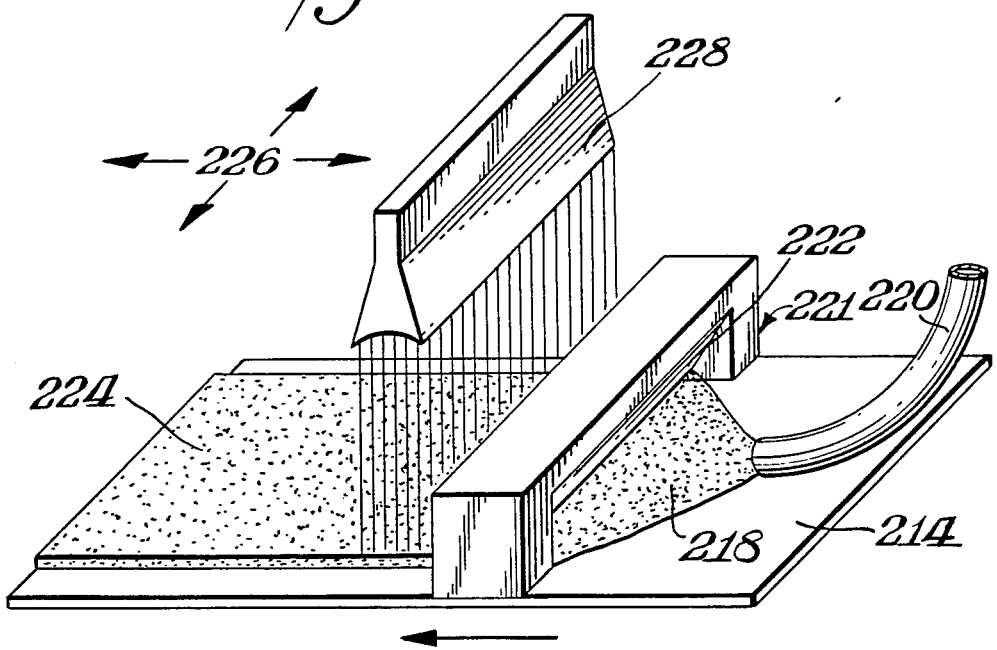
FIG. 15 is a drawing illustrating a continuous coating and polymerization procedure utilizing an inert coating-radiation chamber.

If the monomer-polymer composition has sufficient physical integrity, a coating of predetermined thickness can be made using a doctor knife 222, which is housed in a U-shaped bracket which provides support during gel manufacturing as best seen in FIG. 15. As in FIG. 14, the monomer-polymer composition 218 is pumped by way of a nozzle 220 onto the film support 214. The gel is then formed via the doctor knife 222 and then polymerized by the light source 228, in an inert atmosphere 226. Temperature and humidity must be regulated to prevent solvent loss during coating and irradiation. Both of the methods described above can be used for irradiating thickened monomer solutions or pure water soluble polymer solutions to produce a given gel product 224.

Typical photopolymerization SDS-PAGE formulation for gradient and uniform gels are set forth in Example 1, and for IEF gels in Example 2.

The following example illustrates the preparation of SDS-PAGE electrophoresis gel formulation for preparation of photopolymerization gels using a homogeneous initiating system. The free-radical generating system which includes 4-carboxybenzophenone and the hydrogen donor triethanolamine is particularly preferred.

EXAMPLE 1

Stock solutions were prepared as follows:

MONOMER SOLUTION

Acrylamide: 80 g
N,N'-methylene-bis-acrylamide: 2.1 g
Distilled water to make 200 ml

BUFFER SOLUTION

Tris(hydroxymethyl)amino methane: 18.1 g
Sodium dodecyl sulfate: 0.4 g
Distilled water: 80 ml
pH adjusted to 8.8 w/HCl:
Distilled water to make 100 ml

INITIATOR SOLUTION 4-carboxybenzophenone: 0.90 g
Triethanolamine: 2.00 g
Distilled water: 85 ml
pH adjusted to 8.8 w/HCl or NaOH
Distilled water to make 100 ml

GEL SOLUTION

Gel solutions were prepared by mixng the stock solution as follows,
50% monomer solution
25% buffer solution
25% initiator solution The gel solution was introduced into shallow trays, such as those described above, 4.5"×5" and 12 mils deep. After filling the trays were covered with a polyester film as described above.

SDS-PAGE electrophoresis gels were prepared as indicated above using an exposure time of 60 seconds, and were evaluated for both uniform and gradient exposed samples. Shorter exposure times can be used, but optimum resolution occurred at about 60 seconds using the black light source noted above. These samples were evaluated using a BLR standard mixture of proteins consisting of:
Insulin
Bovin Try, Inhibitor
Cytochrome C
Lysozyme
β-lactoglobulin
α-Chymotrypsinogen
Ovalbumin.

The initiating system so stated yielded gels having good resolving and destaining characteristics. The above protein mixture was resolved into six components by uniform exposure and into seven components for gradient exposed gels; longer exposure times were used for gradient gels to compensate for a neutral density filter when used; in addition gradient exposed gels showed sharper bands. Reproducibility was demonstrated using the formulations so stated.

The following example illustrates the preparation of IEF gel formulations for preparation of photopolymerization gels.

EXAMPLE 2

The following examples illustrate applicability of the compositions of this invention for production gels for isoelectric focusing. Stock solutions were prepared as follows:

STOCK MONOMER SOLUTION

Acrylamide: 6.47 gms
Bis-acrylamide: 0.20 gms
Deionized water to make: 66.7 ml

AMPHOLYTE STOCK SOLUTION

Pharmalyte ® (pH 3 to 10): 2.5 ml
Glycerol: 4.0 ml
Deionized water to make: 10 ml

INITIATOR STOCK SOLUTIONS

Benzoin methyl ether: 0.4 gms
Ethanol: 10 ml
Deionized water to make: 50 ml
Adjust to pH 7.0.

GEL SOLUTION

Gel solutions were prepared by mixing stock solutions as follows:
50% Monomer solution
25% Ampholyte solution
25% Initiator solution.

Gels were prepared as in Example 1. However, exposure times were longer than with SDS-PAGE gels which contain charged initiating species with a minimum of 10 minutes exposure necessary to produce a functional gel. To be assured that polymerization was complete, exposures of 20 minutes using the black light source noted above were made. The longer polymerization however is not due to inefficiency of the initiator but due to the lower acrylamide monomer concentration required for IEF gels (generally 5-7 T/2-5%C vs. 7-30T/2-7% for SDS-PAGE Gels). IEF gels require use of neutral initiating components to avoid interference with pH gradient. Gels with good resolution (a pharmacia standard broad PI calibration kit used) and destaining properties were obtained from solutions prepared as indicated in Example 2. Incorporation of benzoin methyl ether (a neutral initiator that does not require use of a hydrogen donor) was accomplished by addition of ethanol as a co-solvent (5% in gel solution). Ethanol doesn't appear to have adverse effects on electrophoresis.

GEL PRODUCTS 60

Using this invention to induce electrophoretic gel polymerization via photoinitiation it is possible to electrophoretically separate bioorganic molecules using the gel products 60 set forth in the above disclosure by the steps of placing a sample of bioorganic molecules on a thin plate of the gel product and applying a voltage across a dimension other than the thin dimension of the plate. The gel products may vary in thickness from 50 μm to 2 mm with the 100-300 μm range being most preferred. Also, depending upon the desired electrophoretic separation required, the gels may be designed for specific molecular weight or porosity versus distance distributions across a gel or have uniform, lane, or gradient porosity profiles. The advantages of such photopolymerized gels produced in accordance with this invention are summarized as follows:

ACCURATE AND REPRODUCIBLE GELS

The precise control of sample formulation and preparation, light exposure and sample placement affords excellent reproducibility in gel preparation. This translates into high reproducibility of gradient shape and type.

CUSTOM GELS

Gel gradients may be customized to any pattern porosity profile through microprocessor control of light shutter, slit or mask. For example, discontinuous gradients and gradients of complex profiles can be readily produced.

CONTINUOUS PRODUCITON OF GELS

Currently, gels are batch prepared. The instant case allows continuous production. Each gel can thus be made rapidly under reproducible conditions.

THINNER GELS

The photopolymerization process enables the production of thin gradient gels (500μ) which are not readily produced by conventional processes. Since thin gels require less power to run they can be electrophoresed faster and are easier to handle. This is faster and saves energy.

SAFER GELS

Since the user does not have to handle toxic acrylamide, the packaged gel materials can be more safely handled.

STABLE GRADIENT

Unreacted initiators in other systems may cause polymerization of free monomer or cross-linking of polymer to occur after gel preparation is complete. Thus cross-link density and gradient can change uncontrollably. The initiators described herein do not cause polymerization to occur in the absence of light and thus provide a stable electrophoretic gel system.

What is claimed is:

1. A process for preparing a porous gel product, defining a volume, useful for electrophoretic separation the gel product characterized by the presence(d) of a photoinitiator, having a constant atomic composition over its volume, and length and width dimensions, and which is stable, reproducible and has a controlled porosity gradient along one of the length and width dimensions by the steps of:

forming a water solution or dispersion of a mixture of from about 3% weight/volume to about 30% weight/volume of acrylamide monomer and a cross-linking agent, the cross-linking agent comprising about 2% weight/weight to about 15% weight/weight of the total monomer, the crosslinking agent consists essentially of N,N'-(1,2-dihydroxyethylene)-bis-acrylamide, N,N'-methylene-bis-acrylamide (BIS), N,N'-diallyltartramide (DATD), ethylenediacrylate, N,N'-bis-, acrylylcystamine, and polyoxytehyltrimethylolpropane triacrylate (TEOTA)

adding a free radical generating system that absorbs ultraviolet light radiation and initiates polymerization of the monomers, the free radical generating system consists essentially of aqueous soluble or dispersible compounds that include 4-carboxybenzophenone, benzophenone, 9,10-phenanthrene-quinone 3-sulfonate potassium salt, 1,2-napthoquinone-2-sulfonate potassium salt, 1,4-napthoquinone-2-sulfonate potassium salt, 4-trichloromethyl-4-methyl-2,5-cyclohexadienone and other aromatic water soluble or dispersible mono and dicarbonyl compounds, benzoin ethers such as benzoin methyl ether and other benzoins, forming the solution into the shape of the desired gel product, subjecting the formed solution to ultraviolet radiation to polymerize and cross-link the monomer solution or dispersion, and modulating the exposure of the formed solution to the ultraviolet radiation over the length and/or width of desired gel product according the desired porosity gradient.

2. The process set forth in claim 1 wherein the mono and dicarbonyl compounds and dyes are used with hydrogen donors consisting essentially of:
N,N-dimethylaminobenzoic acid,
N,N-dimethylamino ethanol,
N-methyl diethanolamine,
Sodium p-toluene sulfinate, and
Triethanolamine.

3. The process set forth in claim 1 wherein the ampholyte is added to the solution or dispersion and the free radical system contains benzoin methyl ether <0.1% weight/volume.

4. The process set forth in claim 1 wherein the solution is formed into the shape of the gel product by coating the solution onto a substrate.

* * * * *